US00PP34958P2

(12) United States Plant Patent
Dirr et al.

(10) Patent No.: US PP34,958 P2
(45) Date of Patent: Jan. 31, 2023

(54) ***GARDENIA* PLANT NAMED 'ST-07-20'**

(50) Latin Name: *Gardenia jasminoides*
Varietal Denomination: ST-07-20

(71) Applicant: Premier Introductions, Inc., Watkinsville, GA (US)

(72) Inventors: Michael Dirr, Bogart, GA (US); Jeff Beasley, Lavonia, GA (US); Mark Griffin, Watkinsville, GA (US)

(73) Assignee: Premier Introductions Inc., Watkinsville, GA (US)

( * ) Notice: Subject to any disclaimer, the term of this patent is extended or adjusted under 35 U.S.C. 154(b) by 0 days.

(21) Appl. No.: 17/894,365

(22) Filed: Aug. 24, 2022

(51) Int. Cl.
*A01H 5/02* (2018.01)
*A01H 6/76* (2018.01)

(52) U.S. Cl.
USPC ..... Plt./255
CPC ..... *A01H 6/76* (2018.05)

(58) Field of Classification Search
USPC ..... Plt./255
CPC ..... A01H 6/76
See application file for complete search history.

*Primary Examiner* — Anne Marie Grunberg
(74) *Attorney, Agent, or Firm* — Cassandra Bright

(57) ABSTRACT

A new and distinct cultivar of *Gardenia* plant named 'ST-07-20' is disclosed, characterized by fragrant, double white flowers, abundant large flowers in spring with reblooming to fall, lustrous, dark green foliage, columnar growth habit, cold hardy to USDA Hardiness Zone 7. The new cultivar is a *Gardenia*, suitable for ornamental garden purposes.

2 Drawing Sheets

Figure 1:
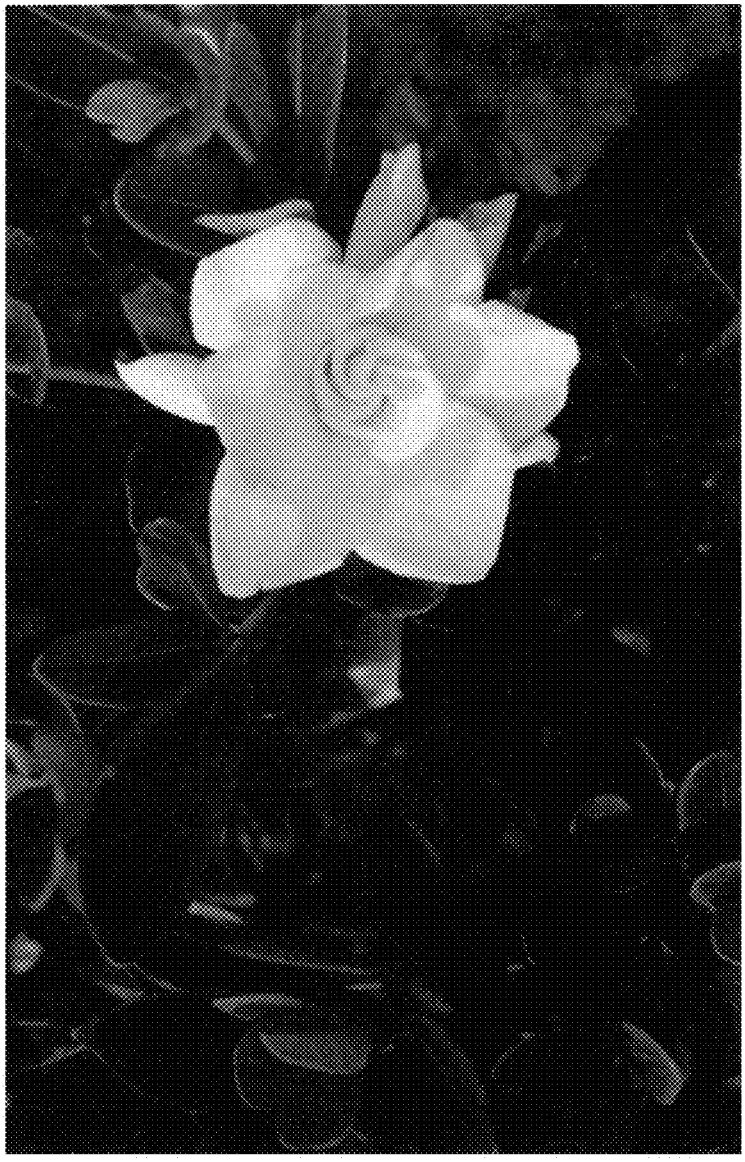

Latin name of the genus and species: *Gardenia jasminoides*.

Variety denomination: 'ST-07-20'.

BACKGROUND OF THE INVENTION

The present invention relates to a new and distinct cultivar of *Gardenia jasminoides*, a member of the Rubiaceae family, hereinafter referred to by its cultivar name 'ST-07-20'. This cultivar is grown primarily as an ornamental for landscape use and for use as a potted plant.

The new *Gardenia* cultivar originated from an open pollination of *Gardenia jasminoides* 'PIIGA-ll', U.S. Plant Pat. No. 27,258, in Watkinsville, Ga., in 2020 and was selected from the progeny by continued evaluation for growth habit, foliage, and floral characteristics.

'ST-07-20' has been asexually reproduced first by softwood cuttings in Watkinsville, Ga. during 2020. This and subsequent propagation of the new variety have shown the characteristics of the cultivar are stable and reproduced true-to-type in successive vegetative generations

SUMMARY OF THE INVENTION

'ST-07-20' has not been observed under all possible environmental conditions. The phenotype may vary somewhat with changes in light, temperature, soil and rainfall without, however, any variance in genotype.

The following traits have been repeatedly observed and are determined to be the unique characteristics of 'ST-07-20' These characteristics in combination distinguish 'ST-07-20' as a new and distinct *Gardenia* cultivar:

1. Fragrant, double white flowers.
2. Abundant large flowers in spring with reblooming until fall. Flowers fade to a soft yellow before turning brown.
3. Lustrous, dark green foliage.

4. Columnar growth habit.
5. Cold hardy to USDA Hardiness Zone 7.

COMPARISON TO PARENT VARIETY

'ST-07-20' is similar in most horticultural characteristics to the seed parent. Plants of the new cultivar 'ST-07-20' however, differ in the following:

1. 'ST-07-20' is more columnar than 'PIIGA-II'.
2. 'ST-07-20' has larger leaves but overall, a smaller plant than 'PIIGA-II'.
3. 'ST-07-20' flowers fade to a soft yellow before turning brown, unlike 'PIIGA-II'.

COMMERCIAL COMPARISON

'ST-07-20' can be compared to the commercial variety *Gardenia* 'PIIGA-I', U.S. Plant Pat. No. 22,510. Plants of the new cultivar 'ST-07-20' are similar to plants of 'PIIGA-I' in most horticultural characteristics, however, plants of the new cultivar 'ST-07-20' differ in the following:

1. 'ST-07-20' has double flowers and abundant reblooming until the fall, whereas 'PIIGA-I' has single flowers and rarely reblooms.

'ST-07-20' is similar in most horticultural characteristics to the commercial variety *Gardenia* 'Crown Jewel', U.S. Plant Pat. No. 19,896. Plants of the new cultivar 'ST-07-20' however, differ in the following:

1. 'ST-07-20' has a columnar habit whereas 'Crown Jewel' has a spreading growth habit.
2. 'ST-07-20' has larger foliage than 'Crown Jewel'.
3. 'ST-07-20' re-blooms from spring to fall, whereas 'Crown Jewel' only flowers in spring.
4. 'Crown Jewel' is less cold hardy than 'ST-07-20'.

BRIEF DESCRIPTION OF THE PHOTOGRAPHS

The accompanying illustrations show characteristics of the new cultivar in photographs as true to color as is reasonably possible to make in illustrations of this nature. Colors in the photographs may differ slightly from the color values cited in the detailed botanical description which accurately describe the colors of the new *Gardenia*.

The accompanying photograph in FIG. 1 illustrates in full color an up-close view of the flower of 'ST-07-20'.

Figure 2:
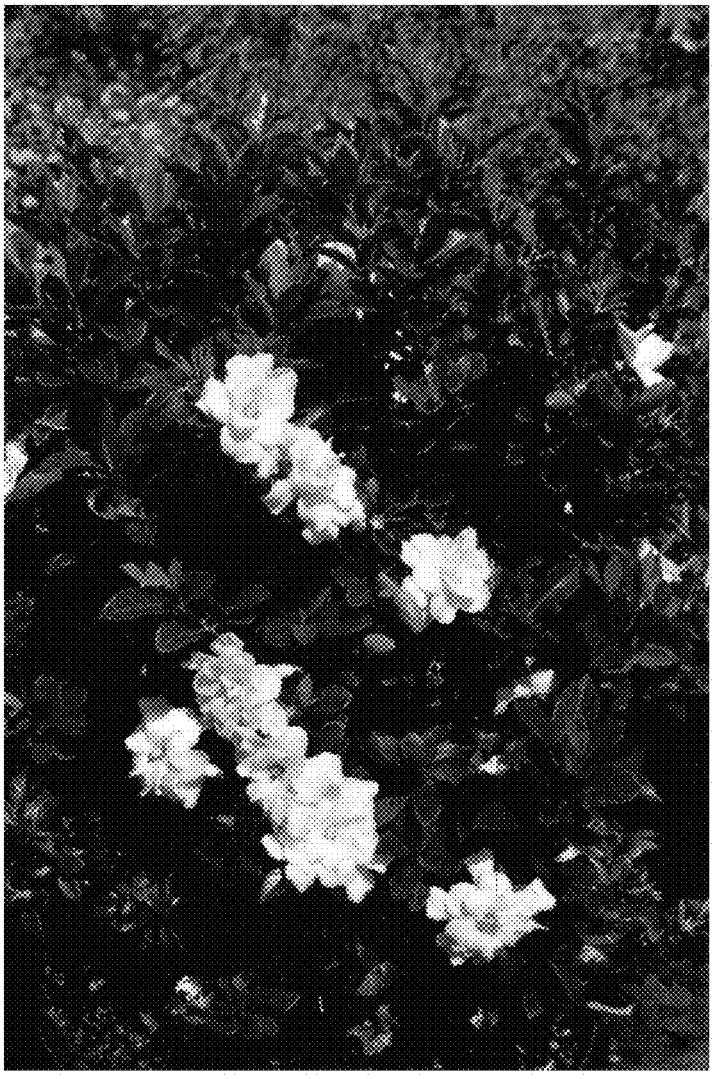

FIG. 2 shows the plant habit of 'ST-07-20'.

DETAILED BOTANICAL DESCRIPTION

In the following description, color references are made to The Royal Horticultural Society Colour Chart 2015 except where general terms of ordinary dictionary significance are used. Plants used for the description were approximately 2 years old and were grown in 3 gallon containers in full sun under outdoor conditions in Watkinsville, Ga. Averages have been applied.

Botanical classification: *Gardenia jasminoides* 'ST-07-20'.

PROPAGATION

Propagation method: Terminal cuttings.

Time to rooting: About 21 days at 32° C. in summer.

Time to produce a rooted plantlet: 4 months at 32° C. in summer.

Root description: Numerous, fibrous, and well-branched. Colored RHS White 155A.

PLANT

Growth habit: Upright, evergreen shrub.

Height: Average 61 cm.

Plant spread: 49 cm.

Branching characteristics: Freely branching.

First year stems:

- *Length.*—15 cm.
- *Diameter.*—3 mm.
- *Shape.*—Terete.
- *Color.*—Young: RHS Yellow-Green 143C. Woody: RHS Brown 201B.
- *Pubescence.*—Finely hairy.
- *Strength.*—Flexible.

Second year stems:

- *Length.*—50 cm.
- *Diameter.*—5 mm.
- *Shape.*—Terete.
- *Color.*—RHS Brown 201B.
- *Pubescence.*—None by second year.
- *Strength.*—Easily broken once mature.

Bark: Some stringy exfoliation beginning on second year stems. Colored near RHS Brown 201B.

Trunk:

- *Diameter.*—1.7 cm at the soil line.
- *Color.*—RHS Brown 201B.

Internode length: 4 cm.

Vegetative bud:

- *Arrangement.*—Opposite.
- *Shape.*—Conical, single-scaled.
- *Length.*—3 mm.
- *Width.*—1 mm.
- *Color.*—RHS Yellow-Green 144C.

FOLIAGE

Leaf:

- *Arrangement.*—Opposite, some whorled, especially at terminal end of shoot.
- *Length.*—5 cm.
- *Width.*—2 cm.
- *Shape.*—Lanceolate.
- *Apex.*—Acuminate.
- *Base.*—Cuneate.
- *Margin.*—Entire.
- *Texture of top surface.*—Glabrous, lustrous.
- *Texture of bottom surface.*—Glabrous, lustrous.
- *Color.*—Young foliage upper side: RHS Yellow-Green 144A. Young foliage under side: RHS Yellow-Green 144B. Mature foliage upper side: RHS Yellow-Green 147A. Mature foliage under side: RHS Yellow-Green 147B.
- *Venation.*—Type: Pinnate. Venation color upper side: RHS Yellow-Green 143A. Venation color under side: RHS Yellow-Green 147C.

Petiole:

- *Length.*—2 mm.
- *Diameter.*—3 mm.
- *Texture.*—Glabrous.
- *Color.*—RHS Yellow-Green 144A, both surfaces.

FLOWER

Bloom period: Spring to frost. Flowers are produced abundantly from May to June, and then sporadically through November in Watkinsville, Ga.

Flowers:

- *Type and habit.*—Flowers are double and borne singly at the terminals and in the axils where two stems divide. Individual flowers are showy for about 2 days and remain on the plant for about 1 to 2 weeks after they have senesced.
- *Height.*—4.5 cm.
- *Diameter.*—7.5 cm.

Bud:

- *Shape.*—Oblong.
- *Length.*—4.5 cm.
- *Diameter.*—1.5 cm.
- *Color.*—RHS Yellow-Green 144A.

Petals:

- *Length.*—3 cm.
- *Width.*—2 cm.
- *Apex.*—Rounded.
- *Base.*—Attenuate.
- *Shape.*—Obovate.
- *Margin.*—Entire, undulating and overlapping in arrangement to form a whorl.
- *Number.*—6 to 8 true petals and 16 to 18 petaloids per flower.
- *Texture.*—Glabrous, both surfaces.
- *Color.*—Upper surface at peak bloom: RHS White NN155C. Under surface at peak bloom: RHS White NN155C. Upper surface, aging: RHS Yellow 11C. Under surface, aging: RHS Yellow 11C. Upper surface before dehiscing: RHS Brown N199D. Under surface before dehiscing: RHS Brown N199D.

Petaloids:

- *Length.*—Average 1.5 to 2.5 cm, becoming smaller toward the top and center of the flower.
- *Diameter.*—Average 1.1 to 2.1 cm becoming smaller toward the top and center of the flower.

*Color*.—Upper surface at peak bloom: RHS White NN155C. Under surface at peak bloom: RHS White NN155C. Upper surface, aging: RHS Yellow 11C. Under surface, aging: RHS Yellow 11C. Upper surface before dehiscing: RHS Brown N199D. Under surface before dehiscing: RHS Brown N199D.

*Texture*.—Glabrous, both surfaces.

Peduncle:

*Length*.—1 cm.

*Diameter*.—4 mm.

*Color*.—RHS Yellow-Green 141A.

*Texture*.—Smooth, glabrous.

*Aspect*.—Upright.

*Strength*.—Strong.

Calyx:

*Length*.—2.5 cm.

*Width*.—1.5 cm.

*Color*.—RHS Green 143A.

Sepals:

*Arrangement*.—Star-shaped calyx with 5 sepals fused at the base.

*Length*.—2.5 cm.

*Diameter*.—4 mm.

*Color*.—RHS Green 141A.

*Texture*.—Smooth, glabrous.

*Shape*.—Lanceolate.

*Apex*.—Acute.

*Margin*.—Entire.

Pedicels:

*Length*.—2 cm.

*Diameter*.—7 mm.

*Texture*.—Glabrous.

*Color*.—RHS Yellow-Green 146B.

REPRODUCTIVE ORGANS

Stamens:

*Number*.—4 to 6, sometimes petaloid or malformed.

*Arrangement*.—There is no separate filament structure present, instead the anthers are fused to the base of the petals.

Anthers:

*Shape*.—Lanceolate.

*Length*.—8 mm.

*Width*.—2 mm.

*Color*.—RHS Brown N199D.

*Pollen*.—Quantity: Scant. Color: RHS Yellow 9A.

Pistil:

*Number*.—1 per flower, inferior.

*Length*.—1.7 cm.

*Diameter*.—5 mm.

*Style*.—Length: 3 cm. Width: 1.5 mm. Color: RHS Yellow-Green 154C.

*Stigma*.—Shape: Obovate. Length: 5 mm. Width: 4 mm. Color: RHS Yellow 6A.

*Ovary*.—Shape: Ellipsoidal. Length: 5 mm. Width: 4 mm. Color: RHS Yellow 2C.

OTHER CHARACTERISTICS

Disease and pest resistance: No specific pest or disease resistance or susceptibility has been observed.

Temperature tolerance: USDA Plant Hardiness Zone Map (2012) Zone 7 to 9.

Fruit/seed production: Not observed to date.

What is claimed is:

1. A new and distinct cultivar of *Gardenia* plant named 'ST-07-20' as herein illustrated and described.

* * * * *